United States Patent
Quaid

(10) Patent No.: US 9,504,380 B1
(45) Date of Patent: Nov. 29, 2016

(54) SYSTEM AND METHOD FOR ASSESSING HUMAN VISUAL PROCESSING

(71) Applicant: Patrick Quaid, Guelph (CA)

(72) Inventor: Patrick Quaid, Guelph (CA)

(73) Assignees: EVECARROT INNOVATIONS CORP., Oakville (CA); Patrick Quaid, Guelph (CA)

( * ) Notice: Subject to any disclaimer, the term of this patent is extended or adjusted under 35 U.S.C. 154(b) by 0 days.

(21) Appl. No.: 14/754,797

(22) Filed: Jun. 30, 2015

(51) Int. Cl.
*A61B 3/08* (2006.01)
*A61B 3/00* (2006.01)
*A61B 3/14* (2006.01)
*A61B 3/113* (2006.01)
*H04N 13/04* (2006.01)

(52) U.S. Cl.
CPC ............. *A61B 3/085* (2013.01); *A61B 3/0025* (2013.01); *A61B 3/113* (2013.01); *A61B 3/14* (2013.01); *H04N 13/0438* (2013.01)

(58) Field of Classification Search
USPC .................................................. 351/200–246
See application file for complete search history.

(56) References Cited

U.S. PATENT DOCUMENTS

| | | | | |
|---|---|---|---|---|
| 2010/0201942 A1* | 8/2010 | Hess | ...................... | A61B 3/022 351/201 |
| 2010/0283969 A1* | 11/2010 | Cooperstock | ........... | A61B 3/022 351/201 |
| 2012/0127426 A1* | 5/2012 | Backus | .................. | A61H 5/005 351/203 |

* cited by examiner

*Primary Examiner* — Mohammed Hasan
(74) *Attorney, Agent, or Firm* — Edgar Chana Law; Aaron Edgar

(57) ABSTRACT

A system and method for assessing visual processing of a human subject is provided that allows measurement of vergence facility among other measurements. The system and method present a sequence of questions on a dichoptic display that request the identification of an item with stereo disparity. The questions alternate between the item having crossed stereo disparity and uncrossed stereo disparity in order to stress the vergence facility by forcing the eyes to diverge and converge to identify the item with stereo disparity. The time period for providing a response can be compared to a normative value that is equivalent to approximately 15 vergence cycles per minute to determine an abnormal or normal vergence facility.

20 Claims, 5 Drawing Sheets

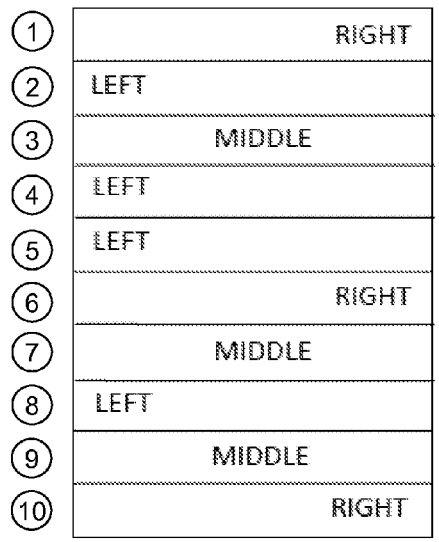
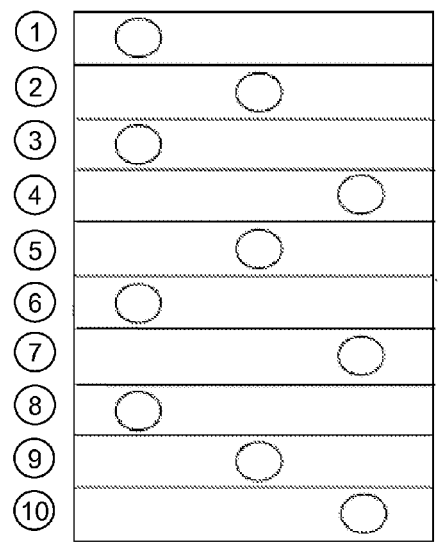
FIG. 2A          FIG. 2B
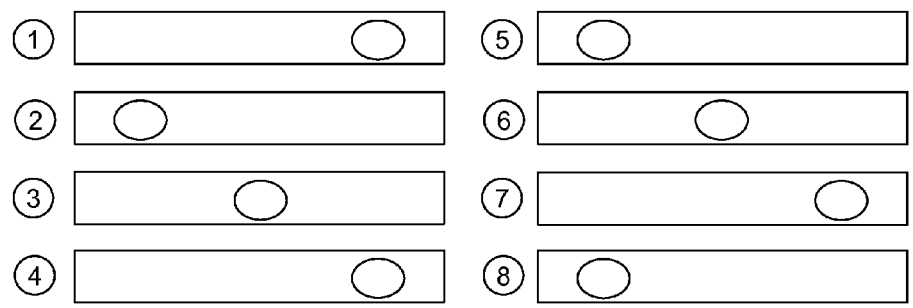
FIG. 2C

SYSTEM AND METHOD FOR ASSESSING HUMAN VISUAL PROCESSING

FIELD

The present disclosure relates generally to systems and methods for combining and integrating sensorimotor, perceptual and cognitive testing of human subjects.

BACKGROUND

Mental chronometry is a measure of cognitive speed and is the actual time taken to process information of different types and degrees of complexity. The basic measurement is the individual's response time (RT) to a visual or auditory stimulus that calls for a particular response, choice or decision.

In order to view visual stimulus accurately a person must use the accommodative system, which changes the shape of the lens in the eye to focus the image on the retina, and the vergence system, which is the system responsible for moving the eyes so that they are properly aimed at the object being viewed. Although both the accommodative and vergence systems are used to view an object, current RT testing does not isolate or stress the vergence system sufficiently.

It is known that many and various screening tests are available to test a subject's vision, hearing, speech, motor, and/or hand and motor coordination, as well as perceptual and cognitive skills. Some of these tests involve complex ideas or include some type of cultural or educational bias making it difficult to administer the same universal test across ages, academic grade level, cultures and groups with minimal degrees of mental processing ability.

Although RT tests appear to be very simple compared to the typical items in psychological tests, they can prove to be of significant value in exposing individual differences related to their sensorimotor, perceptual and cognitive components. Galley & Galley (1999) describe the use of certain features of eye movements as a chronometric method for the study of intelligence quotient (IQ). However, although the method is remarkably simple and efficient, it calls for specialized instrumentation and computer programs.

The King-Devick (KD) test of oculomotility is a tool for evaluation of saccade, or fast movements of the eye, that consists of a series of test cards of numbers or letters. The test cards become progressively more difficult to read due to variability of spacing between the characters. Both errors in reading and speed of reading are included in deriving a score. Apart from being able to recognize and name numbers or letters in a left to right sequence, the test lacks for other, simple and considered important, perceptual and cognitive reading demands. The KD test also does not directly target the vergence system.

SUMMARY

According to a first aspect, a system and method are provided for assessing human visual processing. The system comprises a computing device having a dichoptic display, a processor and a memory, the memory storing instruction to configure the processor to perform the following method steps: present a sequence of questions on the dichoptic display, each of the questions requesting identification of an item with stereo disparity, the questions alternating the item between crossed disparity and uncrossed disparity; receive a response to at least one of the questions; and measure a time period from presenting at least one of the questions to receiving the corresponding response. The dichoptic display can include a video display that is coupled with stereoscopic glasses, such as active shutter glasses synchronized to the video display, for example.

In some aspects the processor can be further configured to compare the time period to a normative value. In other aspects the processor can be configured to measure a total time period to receive responses to the sequence of questions. In a further aspect the processor can be configured to measure a number of vergence cycles over the total time period and compare the number of vergence cycles over the total time period to a normative value to determine an abnormal or normal vergence facility. The normative value can be related to 15 vergence cycles per minute which has been found to be significantly correlated to reading ability.

In some aspects, requesting identification of the item can include identifying a position of the item with stereo disparity. The identification of the position can be any one of left, middle/center, and right, and the response can be any one of left, middle/center, and right. In some aspects the accuracy of the received response can also be measured, and in some aspects feedback can be provided when the response is measured as inaccurate. In related aspects processing image data from a camera can be used for eye-tracking between a crossed state or an uncrossed state, and comparing the eye-tracking to the stereo disparity of the item can be used to objectively assess performance.

In other aspects, the time period or total time period can be stored as a baseline measurement. This can be used to track progression or be used to identify neurological trauma (e.g. a concussion). In some aspects, the time period can be transmitted to a shared database over a communication network.

BRIEF DESCRIPTION OF THE DRAWINGS

For a better understanding of the various embodiments described herein and to show more clearly how they may be carried into effect, reference will now be made, by way of example only, to the accompanying drawings which show at least one exemplary embodiment, and in which:

FIG. 2A is an illustration of an embodiment of a directional word speed reading test;

FIG. 2B is an illustration of an embodiment of a circle speed reading test;

FIG. 2C is an illustration of an embodiment of a horizontal arrangement of test questions that can be used with any of the tests illustrated in FIGS. 2A-B;

DESCRIPTION OF VARIOUS EMBODIMENTS

It will be appreciated that for simplicity and clarity of illustration, where considered appropriate, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather provide a guide to the person of ordinary skill in the art to allow them to make modifications and variations as required.

The embodiments of the systems, devices and methods described herein may be implemented in hardware or software, or a combination of both. Some of the embodiments described herein may be implemented in computer programs executing on programmable computers, each computer comprising at least one processor, a computer memory (including volatile and non-volatile memory), at least one input device, and at least one output device. For example, and without limitation, the programmable computers may be a mobile computing device having at least one network interface. Program code may operate on input data to perform the functions described herein and generate output data.

Figure 1:
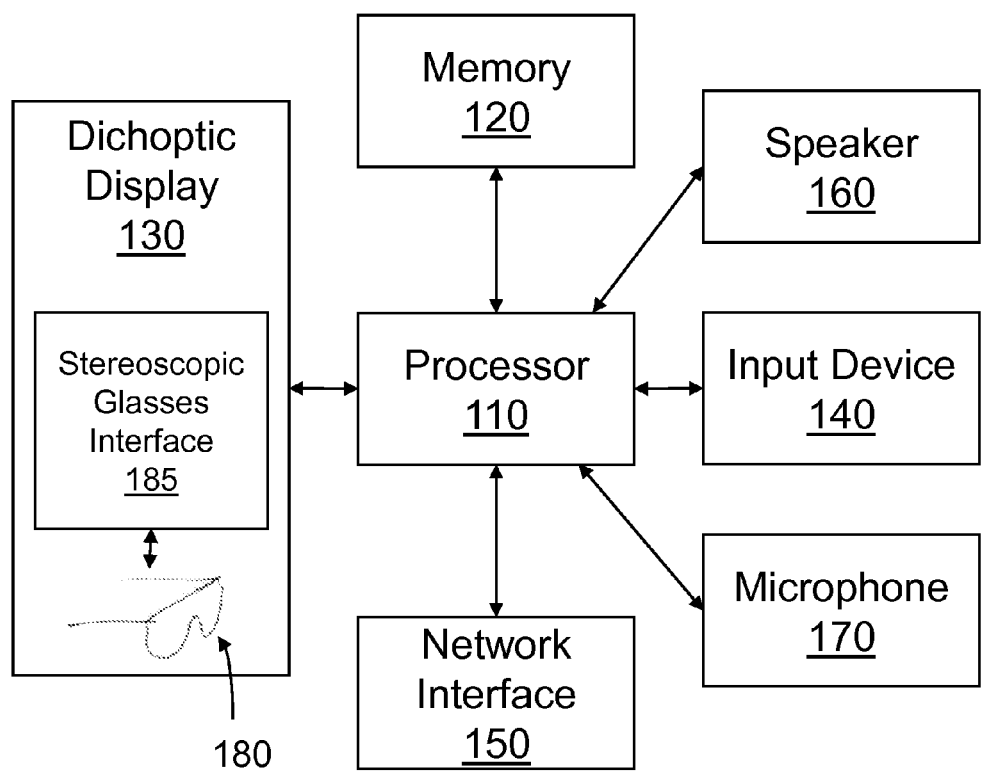
FIG. 1 is a block diagram of a computing device.

Reference is first made to FIG. 1, shown is a block diagram of a computing device 100 that can include a processor 110, memory 120, dichoptic display 130, and input device 140. A network interface 150 can be provided to allow computing device 100 to communicate with other computing devices over a communication network. Computing device 100 can further include a speaker 160 and a microphone 170 for providing audio output and input. Examples of computing device 100 can include mobile computing devices, such as mobile phones, laptops or tablets, and computing devices used in the home, such as a desktop computer, video game console, set top box, or televisions having a processor.

Dichoptic display 130 is a video display that presents a separate and independent image to each eye. Dichoptic display 130 can be used to provide images with stereo disparity, including stereo crossed and uncrossed images. Dichoptic display 130 can include a single video display that is used with stereoscopic glasses 180 or two separate video displays for each eye. In the preferred embodiment a single video display is used to allow testing with and without stereoscopic images (e.g. tests illustrated in FIGS. 2A-C). Stereoscopic glasses 180 are preferably active shutter glasses that operate by alternatively blocking each eye and coordinating the blocking with a normal video display (e.g. a liquid crystal display, light emitting diode display, or other display technology known in the art) to provide alternating left and right eye images. Synchronization of the video display with active-shutter stereoscopic glasses 180 can be provided by stereoscopic glasses interface 185 that provides either a wired or wireless signal (e.g. infrared or radiofrequency, such as Bluetooth). The signal causes stereoscopic glasses 180 to synchronize with alternating left and right eye images provided by a video display. Other embodiments of dichoptic display 130 can use passive stereoscopic systems that include different filters for each eye, such as polarization systems or color anaglyph systems, for example. Other embodiments of dichoptic display 130 can use goggles or a viewer that presents a separate image to each eye. Stereoscopic glasses 180 can alternatively be used to block a single eye to perform monocular testing wherein the subject will be tested using only a single eye with the test images and then retested using the other eye.

In some embodiments, dichoptic display 130 can also include an input device 140 that is integrated with dichoptic display 130, such as a digitizer, to provide a touchscreen interface to computing device 100. Input device 140 could also include other traditional input mechanisms, such as a keyboard and mouse, which can be used with computing device 100. Input device 140 could also be provided as a custom input device that provides larger buttons that correspond with the test responses. For example, a touch pad device or panel with buttons could be provided that included buttons for "left", "middle" (or "center"), and "right". Input device 140 can also include a camera for capturing images of a user in order to receive or validate responses. A camera can also be used with eye-tracking software executing on processor 110 to further validate responses received via another input method.

In some embodiments, stereoscopic glasses 180 can include at least two markers that are separated by a known distance. A camera coupled to computing device 100 can capture one or more images of the test subject wearing the stereoscopic glasses 180. Based on the distance separating the markers in the captured image and the known distance, processor 110 can calculate the distance between stereoscopic glasses 180 and the video display. This measurement can be used to calculate degrees of arc based on the calculated distance and items on the video display. Other embodiments can incorporate distances sensors (e.g. those based on infrared, sonar, or network time of flight) to calculate the distance between the video display and stereoscopic glasses 180. Some embodiments of computing device 100 can also include a gyroscopic sensor to help ensure that the video display is in a fronto-parallel plane with stereoscopic glasses 180.

Processor 110 is configured to control the operation of computing device 100, including coordination between other components coupled to processor 110. Control is provided by execution of software code stored in memory 120. Software code typically includes an operating system, such as Windows, Mac OS X, Linux, iOS, or Android, for example. Computing device 100 can also include any number of application programs stored in memory 120 and configured for execution by processor 110.

Processor 110 can include one or more programmable microprocessors or a microprocessor having more than one microprocessor cores. In addition, processor 110 can include a central processing unit (CPU), memory (in addition to or such as the illustrated memory 120, such as a cache, for example) and an input/output interface through which processor 110 can receive a plurality of input/output signals. Some components of computing device 100 can be integrated with processor 110 and memory 120 in a system on a chip design.

Memory 120 can provide storage for data and software instructions for processor 110. Memory 120 can include both volatile and non-volatile memory. Non-volatile memory (i.e. non-transitory memory) can include flash memory or read-only memory including various forms of programmable read-only memory (e.g. PROM, EPROM, EEPROM). Volatile memory can include random access memory (RAM) including static random access memory (SRAM), dynamic random access memory (DRAM) and synchronous dynamic random access memory (SDRAM).

Speaker 160 is an electric to acoustic transducer that generates sound in response electrical signals provided via processor 110. Speaker 160 can be used to provide guidance and feedback to users of computing device 100. Microphone 170 converts audio signals into electrical signals that can be processed by processor 110. Microphone 170 can provide an alternative input mechanism that allows subjects of computing device 100 to use voice to provide instructions to computing device 100. In some embodiments, microphone 170 can be integrated with or attached to stereoscopic glasses 180.

Network interface 150 allows computing device 100 to connect to communication networks in order to communicate with other computing devices 100. These other computing devices 100 can be servers that are hosted on a local area network or are accessible over a publicly accessible network, such as the internet. Network interface 150 can be wired or wireless. Wireless network interfaces can include those that are compliant with Wi-Fi or Bluetooth standards, or a conventional cellular network interface.

Referring now to FIGS. 2A-C, shown are illustrations of exemplary presentations of questions on video display 130 that request user of computing device 100 to identify an item position. The embodiment of FIG. 2A uses the words "left", "middle", and "right" as the item that can be located in any one of these positions within the rectangle. The embodiment of FIG. 2B uses the position of an object, such as the illustrated circle, within the rectangle for each of the questions. The embodiment of FIG. 2A is referred to herein as the Directional Word Speed Reading (DWSR) test and the embodiment of FIG. 2B is referred to herein as the Circle Location Speed (CLS) test. The embodiment of FIG. 2C illustrates an alternative horizontal arrangement of the questions that can be used with either the DSWR or CLS tests.

Computing device 100 can present questions, such as those illustrated in FIGS. 2A-C, on a video display to a user and receive a response from the user, such as through input device 140 or microphone 170, that identifies the position of the item. The speed to complete the test can be measured by computing device 100 as the time between presentation of the questions on the video display and receiving the correct responses identifying the item positions.

The DWSR and CLS tests are two testing methodologies that can be used to assess the ability to read and/or recognize the spatial concepts of left, middle, and right. The speed with which this can be done has been discovered to be a developmental and age-related skill that is closely correlated to a person's intelligence quotient (IQ). The tests can be used to assess visual perception, neuro-cognitive function, gross and fine motor skills, and also vocal/speech function. The tests can be used to provide diagnostic information with regard to the function and coordination of the visual input and speech language systems. The DWSR and CLS tests the reaction time of the brain circuitry that combines essential sensorimotor, perceptual and cognitive systems of the human-subject at its most basic levels from the youngest possible age onwards.

The embodiments illustrated in FIGS. 2A-C use ten questions on the display at a time. The number of questions that are provided on the video display 130 can be varied in other embodiments to allow providing for a single question or multiple questions at a time. A test subject can be presented with more than ten questions on the display or provided multiple questions by refreshing the display. This can be used to test a subject's endurance to measure for any decline in the time to respond to the questions over time.

The item positions of the questions can be randomly generated to prevent a user from being able to memorize the item positions and the order of questions. It is also preferable that the randomization provides sufficient variation of the item position, such as to prevent an item appearing in the same position too often or too many times consecutively. Other embodiments can also repeat the same randomized questions in order to test memory.

In other embodiments of the DWSR test, the item position may not correspond with the word, thus requiring higher cognitive function from the test subject to correctly identify the item position. For example, the word "left" can appear in the middle position requiring the test subject to separate the concepts of item position with the item word.

The CLS test can be varied by using a different object other than the illustrated circle, such as other geometric shapes, pictograms, etc. In some embodiments, the CLS test can include other objects as noise that can make it more difficult to ascertain the position of the desired item. For example, each question could include a star, a circle and a square, and the test subject would be requested to identify the position of the star.

Figure 2D:
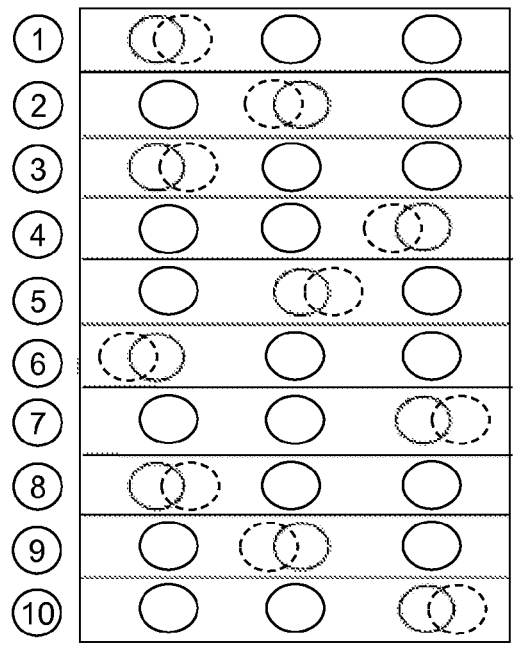
FIG. 2D is an illustration of an embodiment of a stereo acuity test having one of the circles of each question having stereo disparity.

Computing device 100 can be used in conjunction with dichoptic display 130 to test a subject's stereo acuity and vergence facility. This can be used similar to the CLS test of FIG. 2C to determine the location of a circle that is displayed with stereo disparity. FIG. 2D illustrates ten questions in the form of stereograms that each present one circle in stereo disparity form and two circles in regular non-disparate form. FIG. 2D provides the combined left and right eye images that provides the right eye image as a dotted outline for illustration purposes. The sequence of questions alternate the item with stereo disparity between crossed stereo disparity and uncrossed stereo disparity.

Figure 3:
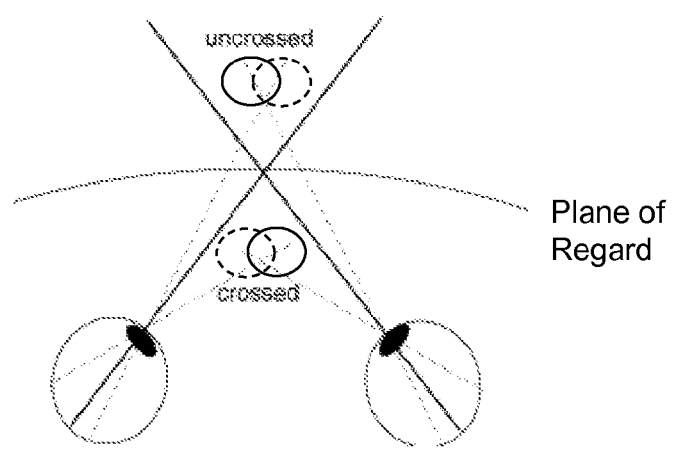
FIG. 3 is a diagram illustrating crossed and uncrossed stereo disparity.

FIG. 3 provides a diagram illustrating the differences between crossed stereo disparity and uncrossed stereo disparity. With uncrossed stereo disparity the left eye views the left offset image (dotted circle) and the right eye views the right offset image (solid circle) so that the object appears behind the plane of regard. Crossed stereo disparity is the opposite with the right eye viewing the left offset image (dotted circle) and the left eye viewing the right offset image (solid circle) so that the object appears in front of the plane of regard. The movement of the eyes to line up both visual axes on the object of regard is referred to as fusion.

A vergence is the simultaneous movement of both eyes in opposite directions to obtain or maintain single binocular vision. When looking at an object with binocular vision, the eyes must rotate around a vertical axis so that the projection of the image is in the center of the retina in both eyes. To look at an object closer by, the eyes rotate towards each other (convergence), while for an object farther away they rotate away from each other (divergence). Referring back to the test illustrated in FIG. 2D, by alternating the questions between crossed disparity and uncrossed disparity the test subjects eyes must repeatedly converge and diverge in order to fuse the stereo image.

Using an alternation in stereo disparity in the exam question sequence incorporates vergence facility into the test without adding any extra test time. The test is more challenging as the eyes are forced to converge and then diverge quickly while proceeding through the sequence of questions to identify the items having stereo disparity. This puts a high demand on the accommodative-vergence complex during the cognitive task again without adding significant extra test time.

The time period from presenting the questions to receiving the responses correctly identifying the item with stereo disparity can be measured by computing device 100. A vergence facility measurement can be obtained for this time period based on the number of questions correctly answered in the time period as each questions requires vergence of the eyes (i.e. alternating convergence and divergence). A normative value has been accepted as approximately 15 cycles per minute at 40 centimeters. The measurement of the time period to receive a response to at least one of the questions and comparing that to a normative value is highly discriminative in determining whether a subject's visual processing system is functioning at its highest level.

Computing device 100 can direct the test subject to wear stereoscopic glasses for testing stereo acuity using the test illustrated in FIG. 2D. The test subject is instructed to select the circle, using voice or touch input for example, that stands out either in front or behind the reference plane in each question. The test can then be repeated with the stereoscopic glasses in the opposite mode so that the left eye image is viewed by the right eye and the right eye image is viewed by the left eye, thus effectively reversing the stereo disparity from crossed to uncrossed.

The position of the item with stereo disparity can differ in each question to minimize the risk of guessing a correct answer. The stereograms shown in FIG. 2D can vary the level of disparity (either per question or per test) to determine the speed of stereo acuity using changes in the level of disparity from 400 seconds and in non-parametric steps to the lowest number of seconds at a working distance of 40 cm and limited by test design. In some embodiments, the test can progressively lower the stereo disparity in each question until the subject is no longer able to discern the correct item.

In other embodiments, the test can be used to measure the number of divergence and convergence cycles per minute with a constant stereoscopic demand. For example, the stereoscopic disparity can be fixed at 100 seconds of arc and each question is alternated between crossed and uncrossed disparity to cause the test subject to converge and diverge their eyes rapidly in sequence.

Similar to the CLS test, the stereoscopic test can be varied to randomize the position of the item with stereo disparity and with three different target designs, that is, single line contour (local stereopsis), random dot (global stereopsis), and with single line contour superimposed on random dot (local and global combined stereopsis) and with crossed disparity so as to see the stereoscopic target in front of the plane of regard, and with uncrossed disparity so as to see the stereoscopic target behind the plane of regard. The background for the test can also vary to include varying amounts of noise, from a clear background to those including increased density of randomly spaced dots. The level of stereo disparity can also vary by question making it more difficult or easier to detect the stereo disparate circle in each question.

Measuring stereo acuity provides a more discriminative measure of overall dynamic visual function than can be provided using a Snellen chart. A measure of 20/10 vision based on a Snellen chart means that the subject can discern down to 150 seconds of arc. By testing stereo acuity using the test illustrated in FIG. 2D and stereoscopic glasses 180 can test more discriminatively and down to 3 seconds of arc depending on the resolution of video display 130 and the distance from stereoscopic glasses 180.

The measure of vergence facility is a very sensitive indicator of reading ability and has been shown to be highly discriminatory between poor readers and efficient readers. Poor reading speed, increased regressions when reading in addition to extra eye movements to read have been found to be highly correlated to vergence facility function. Thus, the vergence facility testing illustrated in FIG. 2D can be used to estimate reading ability to a high degree of confidence and to determine overall whether a test subject is in a normal or abnormal group according to their vergence facility measurement and correlated data on file.

Using the testing methodology illustrated in FIG. 2D provides a rapid screening test that can be used to identify the presence of a learning disabilities or a concussion. The main symptoms of concussion are vision related, including affecting vergence facility. The testing methodology can also be used to define a baseline normal measurement that can be compared with a measurement after a possible concussion. The vergence facility measure can also detect if an athlete is underperforming on purpose to have a lower baseline reading. A baseline reading well-below the normative 15 cycles per minute could indicate purposeful underperformance in an otherwise healthy athlete.

In some embodiments, computing device 100 can further include a camera that can be used with eye-tracking software stored in memory 120 and executed by processor 110. Eye-tracking software can provide an objective verification of whether the subject's eyes can be seen to diverge or converge in accordance with the stereo disparity of the item in the current question.

Figure 4:
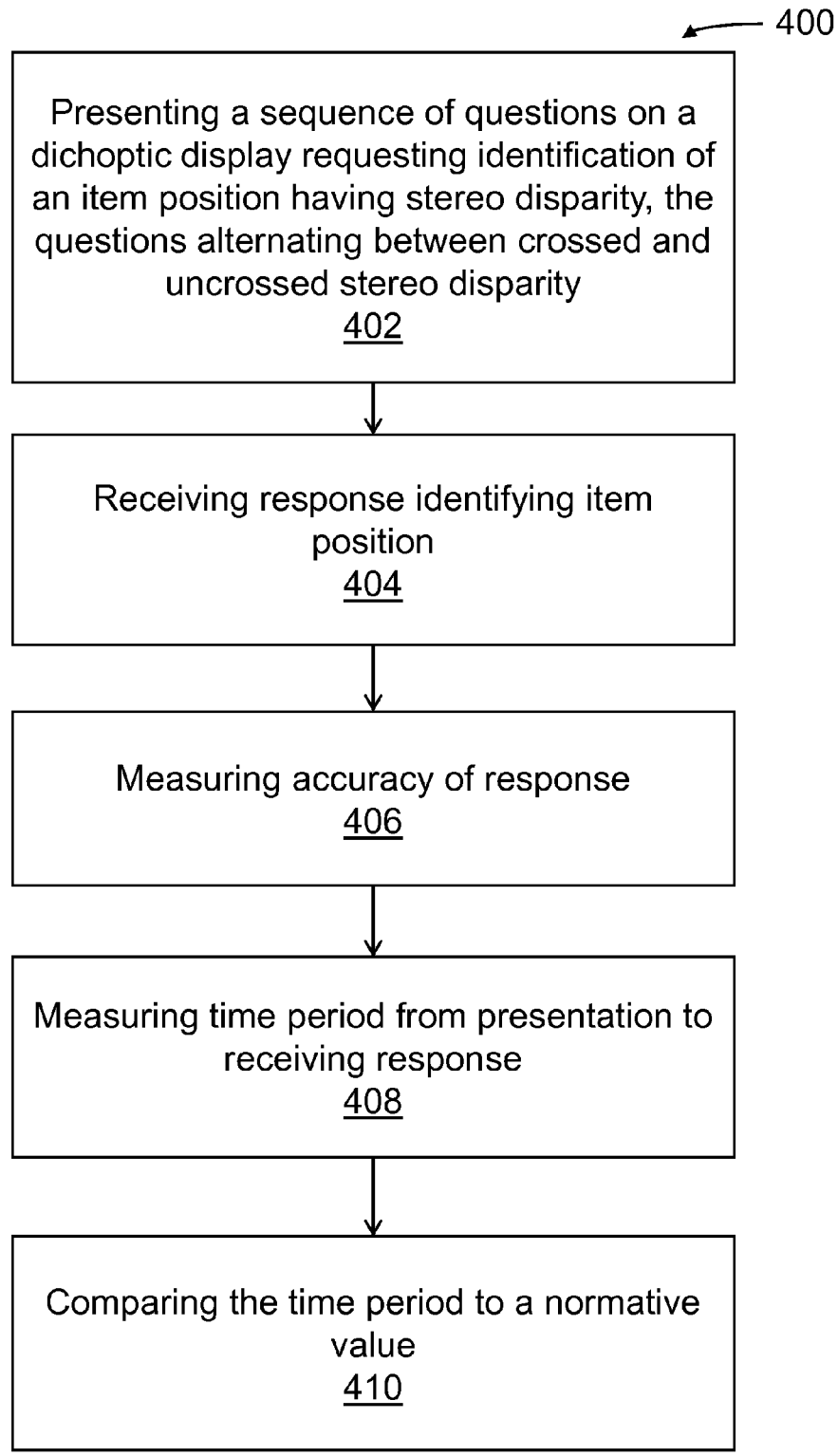
FIG. 4 is a flowchart illustrating a method of screening a test subject using a computing device.

Referring now to FIG. 4, shown is a flow chart illustrating a method 400 for assessing human visual processing. Method 400 can be implemented as a software application executing on processor 110 of computing device 100. For example, method 400 can be provided by an application executing on a tablet or desktop computing device. The application can allow a user to select a language, provide instructions on how to complete the testing provided by the application, and provide a registration function, among other features. In some embodiments, the test subject can also be presented with a questionnaire that can be used to determine levels of symptomatology present. After the test subject has registered, been provided with and understood the instructions, the test subject can initiate the test, for example, by providing a "begin test" input, such through an onscreen button. Initiating the test can begin a countdown after which one or more questions will be presented to the test subject to provide identification of the item position in step 302.

At step 402, the test variant described with respect to FIG. 2D can be displayed on dichoptic display 130. Method 400 provides a timed test and step 402 can further include starting a timer or recording a start time for the test upon presenting the first question on dichoptic display 130.

As provided in the instructions, display of the test requires the test subject to correctly identify the item position for each of the questions as quickly as possible. Stereo acuity tests can use varying levels of stereo disparity (in terms of seconds of arc) to test stereo acuity and vergence facility.

Upon being presented with one or more questions on dichoptic display 130, the test subject must provide answers as quickly as possible. Responses are received identifying the item position in each question in step 404. The test subject determines the position of the item and provides input to the computing device 100.

The response can be received from input device 140, such as buttons on a touch screen or an external keyboard. A touch screen embodiment can include buttons labelled to represent "left", "middle", or "right", for example. Tests carried out with buttons in this manner can provide an indication of visual and motor coordination. The term motor coordination is used herein to refer to hand-eye coordination, or the visual coordination of other body parts, such as the feet for example. In other embodiments, microphone 170 can be used to allow the test subject to vocalize the responses. For example, the test subject must state the question number and identify the item location (e.g. "one left, two middle, three right"). Some embodiments can use both verbal and hand coordinated input from the test subject. These different aspects can be tested sequentially or together so that the test subject must press a button and verbalize the response simultaneously.

Next, at step 406, the accuracy of the response received from the test subject can be evaluated against the questions that were provided in step 402. Processor 110 can compare the input received (e.g. from input device 140 and/or microphone 170) with the question to determine if the test subject provided the correct response. The accuracy determination of the received responses can be used in determining the test subject's score, or to request the test subject re-attempt the question which will extend the time it takes for the test subject to complete the test.

In some embodiments, if an incorrect response is received immediate feedback can be provided that indicates that the test subject had provided an incorrect response and should make another attempt to provide the correct response. Feedback can be provided by video display, speaker 160, vibration motor, or any combination thereof. Examples could include a displaying a red "X" on the video display or making a buzzing sound from speaker 160. The subsequent response from the test subject would then be received at step 404 and re-evaluated at step 406.

At step 408, the time period is measured from the presentation of the one or more questions in step 402 to receiving a correct response in step 404. This can be used to measure the test subject's reaction time. The time period can be measured on a question by question basis, and the time period can also be measured for completion of multiple questions, such as all those displayed on video display at one time or for the entire test. Measuring the time period for each question can measure the variance between answers to determine if the test subject is slowing down during progression of the test. In some embodiments the time period can be measured after receiving the first response to ensure that the eyes are making a full vergence cycle (e.g. from converged to diverged or vice-versa).

Next, at step 410, the measured time period(s) from step 408 can be compared to a normative value. For vergence facility measurements this can include a comparison to 15 vergence cycles per minute. Some embodiments can also use the accuracy determination from step 406 to determine normal or abnormal results. Examples of the time period can include the overall time period for the test or average reaction time for question. Other factors can be used to weight the score of the test, such as whether the test subject's reaction times were increasing or decreasing throughout the test. In some embodiments hand/eye input and verbal input can be tested separately in order to isolate verbal or motor issues.

The comparison in step 410 can also be compared against the test subject's own historic scores or normative values determined from test results of the general population. Computing device 100 can include a table of measurements that can be used for comparison purposes with the test subject's measurements. In other embodiments, a measurement database hosted on a network, such as that described with respect to FIG. 5, can be used to evaluate the test results. The table of measurements can be indexed by groups to determine if the test subject's results are normal for their group (e.g. a normal result for their age or grade level). The grouping can include age, scholastic grade level, age and sex, or age, sex and geographic location, among other factors and combinations.

If it is determined that the test results are outside of the normative values a questionnaire can be provided to the test subjects to determine possible causes for the variance. The questionnaire can provide questions that relate to presence of learning disabilities, the possible occurrence of neurological trauma (e.g. a concussion), or other symptomatology.

Research has shown the DWSR and CLS results to be significantly related to individuals' ages, grades at school and to non-verbal and verbal IQs with very high probability (e.g. P values of 0.0001). The claim is made, therefore, assuming there are no errors of measurement, that the DWSR and CLS are measures of neurological integrity that demonstrate and correlate with higher IQs when the test subjects' performance speeds are faster than those expected for their ages or grades at school. However, when subjects' performance speeds on the DWSR and CLS are slower than those expected for their ages or grades at school, the causes can be numerous. The slowness may result from one or more of a combination of lack of understanding of the tasks required, poor motivation, poor attention span, poor directionality, poor visual acuity, poor ocular motility, poor binocular vision, poor eye-hand coordination, poor language and speech articulation, developmental delay or low IQ.

The value of the DWSR and CLS tests lie in their simplicity of design and very short time of testing (seconds rather than minutes) and their repeatability, which can show training and memory effects. The tests show the importance of knowing the right direction and moving there, which in turn involves spatiotemporal orientation and actions directed by the ability to pinpoint objectives (top down brain functions) and to pinpoint objects in space-time (bottom up body and brain functions). These are crucial to the ways human beings act, function and behave.

Using computing device 100 allows measurements from millions of subjects and to accumulate and process a large database that can be standardized and against which individual differences and performances may be assessed regarding health and disease states, academic and sporting performances, and training and learning protocols. In qualified hands, the measurements therefore should prove to be of significant diagnostic value.

Figure 5:
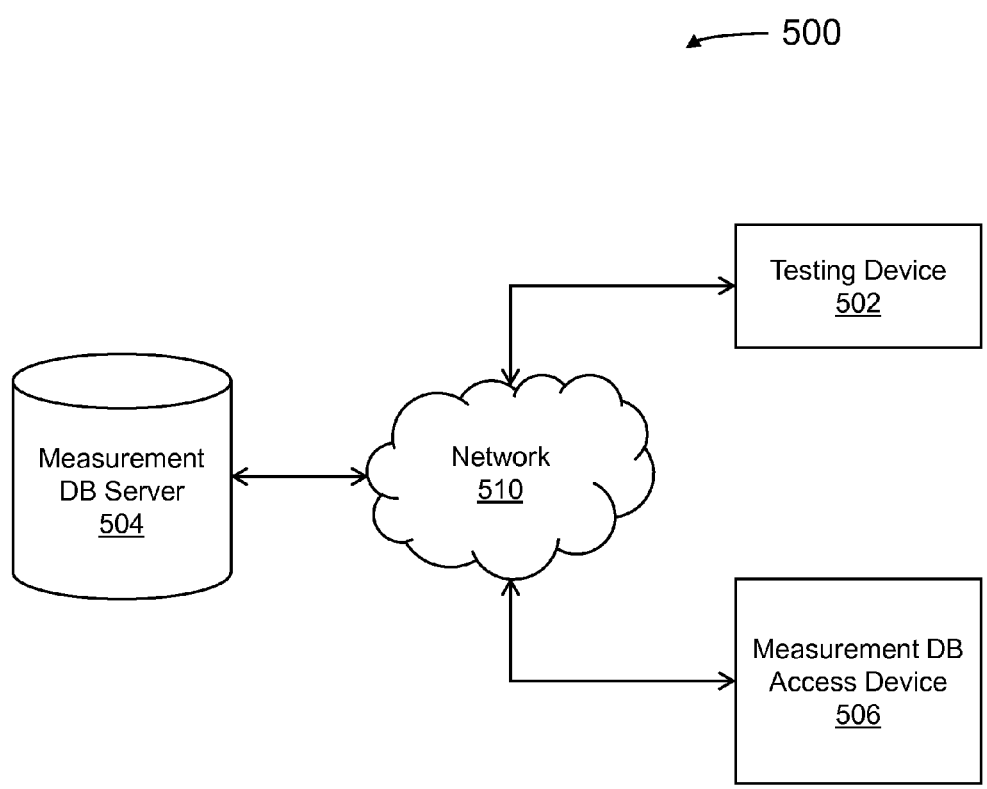
FIG. 5 is a block diagram of a system for providing access to a database of test results from the screening test.

Referring now to FIG. 5, shown is a block diagram of a system 500 for providing access to a measurement database server 504 from any one of testing device 502 and measurement database access device 506 over communication network 510. Testing device 502 can be a computing device 100 that implements that the screening method described in FIG. 4. Measurement database server 504 and access device 506 can also be implemented as computing devices 100, each including a network interface 150 to allow each of the devices in FIG. 5 to communicate over network 510.

Testing device 502 can allow a test subject to register and setup an account with the measurement database server 504. Measurement database server 404 can store account records for each test subject that track aspects such as age, sex, geographic location, and other aspects that may be relevant to a test subject's test measurements. Measurement database server 504 can provide authenticated access using the test subject's user credentials to obtain secure access (e.g. encrypted) between testing device 502 or access device 506. Measurement database server 504 is a shared database that can also allow a test subject to share their test results with the account of a health care practitioner to monitor and evaluate therapeutic performance. Measurement database server 504 can also store the results of any questionnaire administered by testing device 502.

When a test subject completes a test (or series of tests) using testing device 502 the results can be provided to measurement database server 504. The results can include a calculated overall score or provide a detailed response time to each question. Measurement database server 504 can store the test results in a private database associated with the test subject.

In some embodiments, testing device 502 can further include a method of accepting manual entry of time to complete a test or series of tests. This can allow for non-electronic testing results to be gathered and provided to measurement database server 504. These manual results can be flagged as a "manual entry" so that this statistical relevance can be used when analyzing the measurement database.

The private database can be used to compare a test subject's historic results. This can be useful to determine if a test subject's condition is improving or degrading. Applications can include monitoring therapeutic performance to ensure that measurements are improving towards an acceptable range. The private database can also include a baseline test result that can be used to evaluate whether the test subject had sustained a concussion. Historic data can also be used to determine progression or diagnosis of any degenerative disease or progression of neurological or neuromuscular disorders.

In some embodiments, measurement database server 504 can also anonymize the test results and store these results in a publicly shared database. Anonymizing the test results can include removing all personal identifying information but including aspects that can be relevant to the test score, such as age or sex, among other factors. Test results in the public database can be used to compare a test subject's results with norms particular to the test patient. Standard deviation analysis can be performed on the public database to determine these norms for certain classes based on a number of factors, including, but not limited to, age, sex or geographic location. The public database test results can also be used for research and analysis purposes.

Questionnaire data provided by test subjects can also be used to separate public results into normal databases and abnormal databases. For example, test results can be separated based on a pre-existing medical condition, concussive events, medications, learning disabilities, among others.

Measurement database server 504 can be provided using a high availability web server, such as Nginx, for example, and a database management system, such as Postgre SQL, for example. Communication network 510 can include the internet and measurement database server 504 can be secured using a firewall. Communication with measurement database server 504 can be provided over secure socket layer (SSL) protocol, or using other known encryption methods. These can allow measurement database server 504 to be provided as a secure web service to testing device 502 and access device 506.

Access device 506 can include a computing device 100 with a specific application or a general web browser for connecting with measurement database server 504. Access device 506 can be used by patients and practitioners to monitor progress and therapeutic conformance. Patients can receive a request or offer to share the private test results with a health care practitioner to allow the practitioner using access device 506 to view results of a patient stored in measurement data server 504. Measurement database server 504 can analyze a test subject's private data in order to present information in a manner that is diagnostically useful to the health care practitioner. Typically, this would involve a comparison to normal test results obtained from the public database.

While the exemplary embodiments have been described herein, it is to be understood that the invention is not limited to the disclosed embodiments. The invention is intended to cover various modifications and equivalent arrangements included within the spirit and scope of the appended claims, and scope of the claims is to be accorded an interpretation that encompasses all such modifications and equivalent structures and functions.

The invention claimed is:

1. A system for assessing human visual processing, the system comprising:
    a computing device having a dichoptic display, a processor and a memory, the memory storing instruction to configure the processor to:
        present a sequence of at least two questions on the dichoptic display, each of the questions requesting identification of an item with stereo disparity, the questions alternating the item between crossed disparity and uncrossed disparity;
        receive responses to the sequence of at least two questions;
        measure a total time period to receive the responses to the sequence of questions; and
    measure a number of vergence cycles over the total time period and compare the number of vergence cycles over the total time period to a normative value to determine an abnormal or normal vergence facility.

2. The system of claim 1, wherein requesting identification of the item is identifying a position of the item with stereo disparity.

3. The system of claim 2, wherein identification of the position can be any one of left, middle, and right, and the response can be any one of left, middle, and right.

4. The system of claim 1, wherein the processor is further configured to measure the accuracy of the received responses.

5. The system of claim 4, wherein the processor is further configured to provide feedback when at least one of the responses is measured as inaccurate.

6. The system of claim 1, the system further comprising a camera and the processor is further configured to process data from the camera for eye-tracking between a crossed state or an uncrossed state, and comparing the eye-tracking to the stereo disparity of the item.

7. The system of claim 1 wherein the total time period is stored as a baseline measurement.

8. The system of claim 7, the system having a network interface to transmit the baseline measurement to a shared database over a communication network.

9. The system of claim 1 wherein the dichoptic display comprises a video display coupled with stereoscopic glasses.

10. The system of claim 9 wherein the stereoscopic glasses are active shutter glasses synchronized with the video display.

11. A method of assessing human visual processing, the method comprising:
    presenting a sequence of at least two questions on a dichoptic display, each of the questions requesting identification of an item with stereo disparity, the questions alternating the item between crossed disparity and uncrossed disparity;
    receiving responses to the sequence of at least two questions; and
    measuring a total time period to receive the responses to the sequence of questions;
    measuring a number of vergence cycles over the total time period; and comparing the number of vergence cycles over the total time period to a normative value to determine an abnormal or normal vergence facility.

12. The method of claim 11 wherein requesting identification of the item is identification of a position of the item with stereo disparity.

13. The method of claim 12 wherein identification of the position can be any one of left, middle, and right, and the response can be any one of left, middle, and right.

14. The method of claim 11 further comprising measuring the accuracy of the received responses.

15. The method of claim 14 further comprising providing feedback when at least one of the responses is measured as inaccurate.

16. The method of claim 14 further comprising processing image data from a camera for eye-tracking between a crossed state or an uncrossed state, and comparing the eye-tracking to the stereo disparity of the item.

17. The method of claim 11 further comprising storing the total time period as a baseline measurement.

18. The method of claim 17 further comprising transmitting the baseline measurement to a shared database over a communication network.

19. The method of claim 11 wherein the dichoptic display comprises a video display coupled with stereoscopic glasses.

20. The system of claim 19 wherein the stereoscopic glasses are active shutter glasses synchronized with the video display.

* * * * *